United States Patent [19]

Spencer

[11] Patent Number: 4,619,642
[45] Date of Patent: Oct. 28, 1986

[54] STERILE, COLD CUT CONNECTION PROCESS, APPARATUS AND SYSTEM

[75] Inventor: Dudley W. C. Spencer, Wilmington, Del.

[73] Assignee: E. I. Du Pont de Nemours and Company, Wilmington, Del.

[21] Appl. No.: 711,053

[22] Filed: Mar. 12, 1985

[51] Int. Cl.⁴ .................. A61M 25/00; A61M 1/00
[52] U.S. Cl. ................................. 604/29; 604/283; 604/905
[58] Field of Search .......... 604/29, 244, 280, 283, 604/905; 156/152, 158, 159, 296, 502, 503, 251, 358, 304.2, 304.3, 304.5, 433

[56] References Cited

U.S. PATENT DOCUMENTS 4,219,221 8/1980 Webb ............................ 604/244
4,288,266 9/1981 Konrad et al. ................. 156/304.2
4,412,835 11/1983 Spencer ......................... 604/905
4,443,215 4/1984 Smith ............................ 604/905
4,501,630 2/1985 Kluchi .......................... 156/304.3
4,507,119 3/1985 Spencer ......................... 604/905

Primary Examiner—C. Fred Rosenbaum
Assistant Examiner—Michelle N. Lester

[57] ABSTRACT

A process, apparatus and system for making a sterile connection between thermoplastic tubes. A section of each tube is flattened and a cutting means is urged through the flattened sections. The tubes are aligned with each other and then the cut tube ends are melted, sterilized, and urged together to form a joint between the tubes for each pair of tube ends to be connected. Each joint is cooled and then subjected to light stress to open the temporary seal in each tube, thereby providing fluid communication therethrough.

31 Claims, 8 Drawing Figures

STERILE, COLD CUT CONNECTION PROCESS, APPARATUS AND SYSTEM

BACKGROUND OF THE INVENTION

1. Field of the Invention

This invention relates to a process, apparatus and system for forming a sterile connection (sterile docking) between two tubes.

There are a number of medical and scientific procedures which require the sterile transfer of fluids from one container to another. An example of the need for sterile docking is in continuous ambulatory peritoneal dialysis (CAPD). The CAPD patient has a tube connected to his or her peritoneal cavity via an implanted catheter. A tube from a bag of fresh dialysis solution is connected to the patient's tube. The fresh dialysis solution is drained from the bag into the patient's peritoneal cavity where it remains for about 3 to 4 hours. After this treatment period, the spent dialysate is drained back into the empty bag which is then disconnected from the patient's tube. A bag of fresh dialysis solution is then connected to the patient's tube and the procedure is repeated.

Sterile connections during CAPD procedures would minimize the occurrence of peritonitis. The process, apparatus and system of this invention can be employed with various medical devices including catheters, urinary drainage bags, treatment bags such as those used in IV therapies for administering antibiotic, bacteriostat, or other medication, as well as for sterile connections involving blood bags. At present, blood from a donor is drawn into a primary bag which can be joined to one or two satellite bags, all connected and sterilized before use. These satellite bags can be used for holding blood separated components, such as plasma or platelets; treating agents, such as bases, buffers, stabilizers for cell metabolism, other preservatives, or rejuvenants; or washes to remove a treating agent or other contaminant. The process, apparatus and system of this invention permits blood processing without compromising sterility, limiting storage life, or requiring the preconnection of a multitude of bags, all wet-sterilizable, without knowing which, if any, will be used.

2. State of the Art

U.S. Pat. No. 4,369,799 (Spencer) discloses a process, apparatus and system for sterilely connecting two sterile, closed end tubes. The process comprises urging a hot cutting means through each tube and simultaneously forming a continuous molten seal between a heated cutting surface and a transverse section of each said tube thereby maintaining a seal between the interior and exterior of the tubes, aligning the tubes with each other and joining the respective molten ends of the tubes together to form a joint between the tubes, both while maintaining said seal. The apparatus comprises a cutting means, means adapted to heat said cutting means, a pair of mounting blocks adapted to receive and hold two tubes to be joined, means to provide movement between said blocks and said cutting means to a position such that the cutting means is between said blocks and traversing where the blocks are adapted to receive tubes, means adapted to realign said blocks to a position where two different tube ends are aligned with and facing each other, and means to separate said blocks and the cutting means while urging the blocks together. The patent teaches that during the connection operation there should be no significant visible deformation of the tubes and that, in order to obtain a secure dock, the tubes to be joined must not contain more liquid than a thin film on the walls at or near the locations where they are to be cut and joined.

U.S. application Ser. No. 599,324, filed on Apr. 12, 1984, discloses a process, apparatus, and system for the sterile connection of closed end tubes (flat tube welding). The process comprises flattening a section of each tube to urge inside walls of each tube into contact, urging a hot cutting means through the flattened section of each tube thereby temporarily sealing together the inside walls of each tube and providing molten tube ends, aligning the tubes to be connected with each other, joining the desired molten ends of said tubes together to form a joint between said tubes, and cooling said joint and then subjecting it to stress to open the temporary seal in each tube, thereby providing fluid communication between the joined tubes.

SUMMARY OF THE INVENTION

This invention concerns a method for joining thermoplastic tubes together transversely of the axis of each tube comprising:

(i) flattening a section of each tube to urge inside walls of each tube into contact.

(ii) cutting through the flattened section of each tube.

(iii) separating and aligning the tubes to be connected with each other, (iv) heating the cut ends of the aligned tubes to a temperature sufficient to effect sterilization and to melt them, (v) joining the molten ends together, and (vi) cooling the joint and effecting fluid communication therethrough. Although steps (i) to (vi) are recited in sequence, they need not be practiced sequentially. For instance, step (iv) heating can be accomplished before, during or after step (iii) separation and alignment of tubes cut in step (ii).

This invention also concerns an apparatus for forming a sterile connection between thermoplastic tubes comprising a cutting means, a pair of mounting blocks adapted to receive, hold and flatten the tubes to be joined, means to provide movement between said blocks and said cutting means to a position such that the cutting means is between said blocks and traversing where the blocks are adapted to receive said tubes, means adapted to realign said blocks to a position where two different tube ends are aligned with and facing each other for each pair of tubes of be joined, means to separate the cutting means from the tubes that have been cut, means for heating the cut ends of the tubes, and means for urging together the tubes to be joined.

This invention also concerns a sterile connection system for urinary drainage in which a first drainage container is connected to a drainage tube extended from a catheter implanted in a patient's urethra, wherein the improvement comprises (a) a second drainage container having a connector-free tube specifically for sterile connection and with a sealed distal end, both containers being disposable; and (b) a pair of mounting blocks adapted to receive, hold and flatten the drainage tube and the connector-free tube, cold-cutting means, means to provide a movement between said blocks and said cutting means to a position such that the cutting means is between said blocks and traversing where the blocks are adapted to receive said tubes, means to realign said blocks to a position where the resulting different tube ends to be joined are separated and aligned with and facing each other, means to separate the cutting means from the tubes that have been cut, means for heating the cut ends of the tubes, and means for urging together the tubes to be joined.

This invention also concerns a connector system for continuous ambulatory peritoneal dialysis wherein a catheter is surgically implanted in a patient's peritoneal cavity, comprising (a) a catheter having a thermoplastic tube at one end, the other end being implanted in a patient, the thermoplastic tube being adapted for connection to a medical device outside the patient, the connection being made via (b) a thermoplastic tube adapted for connection to (a) at one end, tube (b) being an integral part of the medical device; alternatively, connection to the medical device made via (c) a thermoplastic tube adapted for connection to (a) at one end and to tube (b) at the other end; (d) a pair of mounting blocks adapted to receive, and flatten thermoplastic tubes (a) or (c), and (b); (e) a cutting means; (f) means to provide movement between said blocks and said cutting means to a position such that the cutting means is between said blocks and traversing where the blocks are adapted to receive said thermoplastic tubes (a) or (c), and (b); (g) means to realign said blocks to a position where different tube ends are aligned with and facing each other; (h) means to separate said blocks and said cutting means; (i) means for heating the tube ends; and (j) means for urging said blocks together.

This invention also concerns an improved catheter for continuous ambulatory peritoneal dialysis, the improvement comprising a thermoplastic tube sterilely attached to the catheter at one end of said tube, the other end of said tube being sealed by fusion of its material.

This invention also concerns an administration set for a catheter for continuous ambulatory peritoneal dialysis comprising a thermoplastic tube having one end adapted for connection to a cathether, said thermoplastic tube being sterilely sealed at its distal end by fusion of its material or, optionally, having a spike at its distal end. It is preferred that the sterile seal be may be thermal fusion.

This invention is characterized in that the cutting means cuts cold and is extensively reusable. The heating means does not contact the thermoplastic tubing, does not pick up any of the material from which the tubing is made and is, likewise, extensively reusable.

DETAILS OF THE INVENTION

Figure 1:
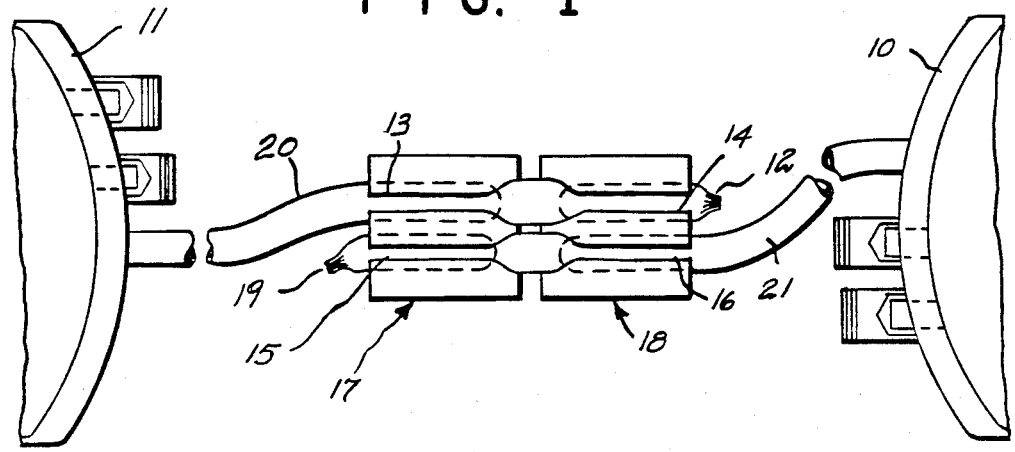
FIG. 1 is a plan view of mounting blocks used to hold two flattened tubes which are to be joined in the starting position.

The tubing employed in the process of this invention is preferably a thermoplastic resin which melts at least 30° C. below the temperature at which it begins to degrade in the time exposed to heat in the process of the present invention. The tubes to be connected are preferably of the same diameter but can have different diameters so long as a complete seal having about 50% of the original tube strength can be made. The tubes to be joined can be made of the same material or can be made of compatible resins. "Compatible resins" as used herein means that at the operating temperature both form thick, viscous melts which will flow together to form a single melt phase without polymer degradation or formation of thermal or other chemical reaction products which would weaken or otherwise interfere with formation of the single melt phase and its subsequent cooling and solidification to a strong joint. For example, polyethylene is compatible with polyethylene copolymers and polypropylene. Candidate materials include polyvinyl chloride, polyurethanes, nylon, polyester thermoplastics such as polyethylene terephthalate, and polyolefins.

In a preferred embodiment of this invention, the tubes to be joined are flattened in an appropriate section so that the inside walls meet. Then the tubes are sequentially or simultaneously cut. Cutting can be effected by any typical cutting implement such as wire, blade, knife, scissors and the like. The tubes will be cut "cold" meaning that they will not be heatdeformed in any substantial way by the action of the cutting means. The cutting means will not be heated to a bacteria-kill temperature and, consequently, the tubes will not be sterilely cut as in Spencer, U.S. Pat. No. 4,369,779. The tubes ends are moved into alignment after cutting and they are melted, sterilized, and subsequently pushed together to form a joint. The joint is briefly cooled and then can be subjected to slight transverse stress (if needed) to open the temporary seal in each tube. The joint is sound and strong and a number of additional joints can be made in subsequent sterile connections with the same tube. Furthermore, each subsequent connection can be made at exactly the same point on the tube. The process can be used to make more than one joint at a time by using multiple (more than two) tubes and multiple tube slots.

The heating means employed, after cold-cutting, is positioned near the tube ends, for a period of time sufficient to raise the temperature of the cut tube ends high enough to effect sterilization and melting, e.g., about 260° C. for one-half second or more. That temperature must be maintained at the ends and as far along the tube (internally) as may have been compromised by contamination. In the apparatus of this invention, the tubes are usually clamped flat at a point beginning about 0.25 to 0.50 cm from the cut end. Thus, the hot wire, fluid jet or other means used to effect the heating should be adapted to transmit heat for a distance of about 0.50 cm within the time/temperature parameters already described. The time between the cold cut and heat sterilization will depend on the environment. It is preferred that heat sterilization be initiated within about 1 or 2 seconds after the cold cut.

Sterilizing means can be any hot surface, solid or liquid, which will radiate heat to the tube, or it can be a jet of hot fluid which heats the tube by conduction. A fluid jet stream of hot air, nitrogen, or the like, would be directed across the ends of the tubes so the hot gas is in contact with the ends. A hot wire or ribbon is preferred because it can be heated quickly as needed with very little electrical energy and easily positioned and controlled. A typical wire would have a diameter of about 2 mms, be heated to a visible red heat of about 400° to 650° C. and held about 0.10 to 0.25 mm from the tube ends for about 3 seconds. Depending upon the wire's distance from the tube ends and its temperature, the time to effect sterility may vary above or below 3 seconds, i.e., about 2 to 15 seconds.

The tubes to be connected in the process of the invention have closed ends in the sense that the tubes are connected to containers such as a blood bag or dialysis bag, to a catheter implanted in a patient, or to some other medical instrumentation closed to the external environment. The present process will work with opened-end tubes but, in that use, will of course, not provide the advantage of sterility or isolation from the environment.

Referring now to FIG. 1, the sealed end 12 of thermoplastic tube 20 is inserted in partial slots 13 and 14, machined in blocks 17 and 18. The sealed end 19 of tube 21 is inserted in partial slots 15 and 16, machined in blocks 17 and 18. Partial slots 13–14 and 15–16 extend the length of blocks 17 and 18, respectively, except for about 1/16 of an inch at the inner facing edges and are aligned to receive straight tubing ends. The partial slots diminish in depth as the inner edge of each block is approached. The upper portions of blocks 17 and 18, for simplicity, are not shown. The tubes are shown in the flattened state which results when the two portions of each mounting block are closed. In FIGS. 1 to 4, tubes 20 and 21 are connected to blood bags 10 and 11. Alternatively, one of said tubes can be connected to a dialysis bag and the other to the patient's peritoneal cavity. Also, the tube which is connected to the patient's peritoneal cavity can be connected at the other end to a bag in lieu of having a sealed end.

Figure 2:
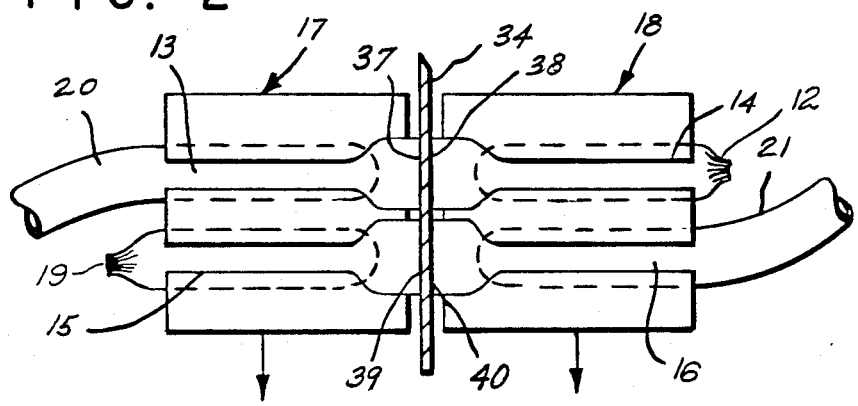
FIG. 2 is a plan view of two flattened tubes being severed by a cold-cutting means.

Referring now to FIG. 2, the cold-cutting means 34, which in the Figure is a blade of steel, has severed tubes 20 and 21.

Figure 3:
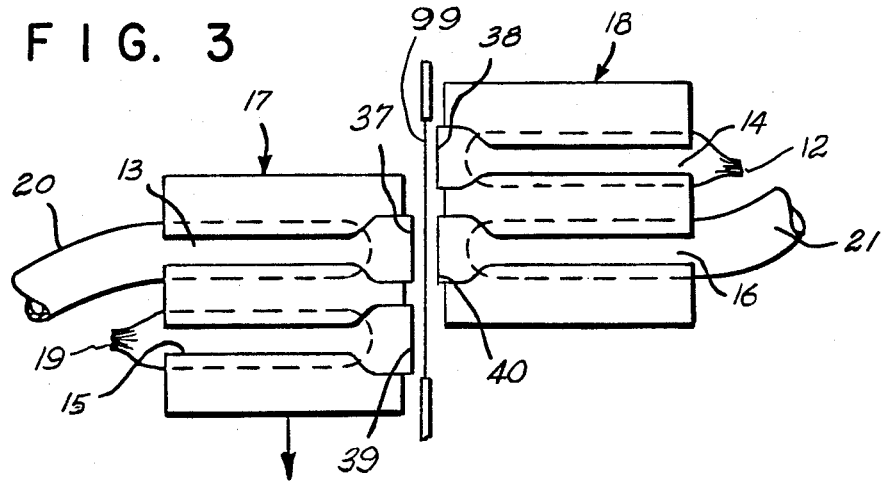
FIG. 3 is a plan view of two flattened tubes being repositioned, aligned opposite each other and being hot wire-melted and sterilized.

Referring now to FIG. 3, block 17 has been moved relative to block 18 so that partial slots 13 and 16 along with tubes 20 and 21 are aligned. A hot wire, 99, is positioned near the severed ends of the tubes, but not touching them. The wire transmits heat to the tube ends sufficient to sterilize the tubes and to melt tube ends preparatory to the joining step wherein molten ends are urged together and integrally connected. The Figure shows temporary seals 37–38 and 39–40 sealing shut the separated portions of tubes 20 and 21, respectively. Seals 37–38 and 39–40 are created by the melting together of the inner walls of tubes 20 and 21 in the vicinity of hot wire, 99. These molten temporary seals 37, 38, 39 and 40 prevent exchange of air or other fluid between the interior of tubes 20 and 21 and the immediate outside environment of the tubes as well as contamination from particles suspended in the air or on the tubing or apparatus surface.

Figure 4:
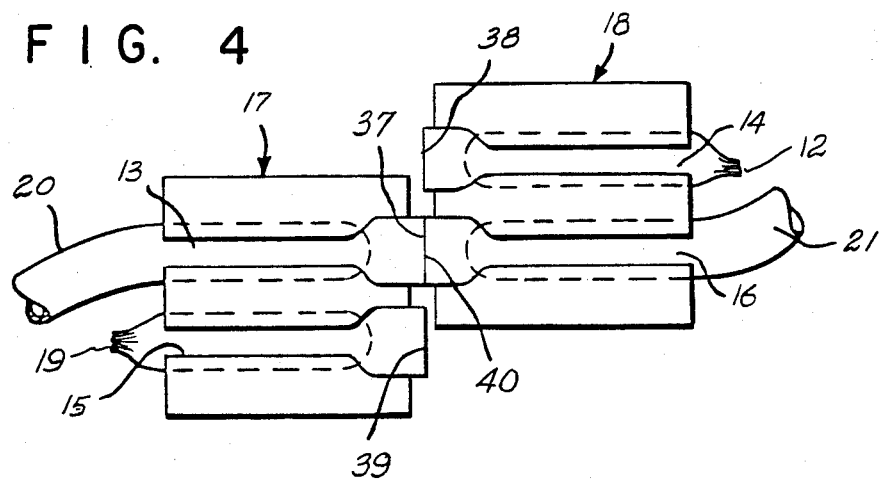
FIG. 4 is a plan view of tubes 20 and 21 whose ends, 37 and 40, have been joined.

Referring now to FIG. 4, ends 37 and 40 are shown in a joint caused by urging blocks 17 and 18 together.

Figure 5:
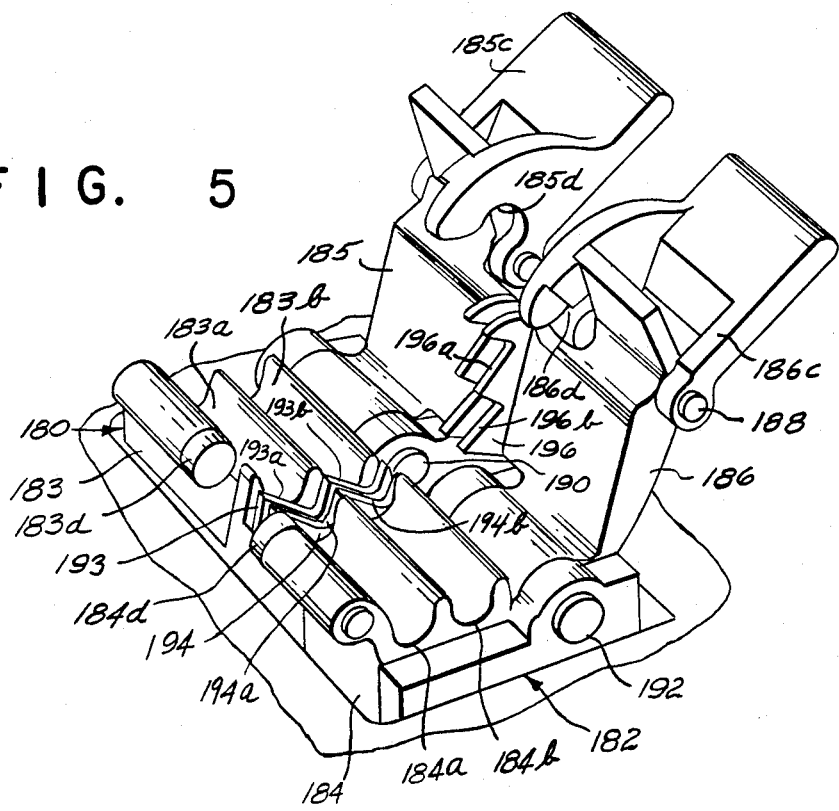
FIG. 5 is a perspective view of a typical mounting block configuration.

Referring now to FIG. 5, mounting blocks 180 and 182 are designed for flattening the tubes in a diagonal plane. The tube mounting blocks 180 and 182 include covers 185 and 186 pivotally attached at hinge points 190 and 192 to tube holder bases 183 and 184. Slots 183a and 183b are provided in mounting block 180 and slots 184a and 184b are provided in mounting block 182 for holding the tubes to be spliced. At the inside facing ends of slots 183a, 183b and 184a, 184b are jaws 193 and 194, respectively. Jaw 193 has flat surfaces 193a and 193b and jaw 194 has flat surfaces 194a and 194b for flattening the tubes when the upper and lower halves of each mounting block are closed. Cover 186 of mounting block 182 has a corresponding jaw 196 with flat surfaces 196a and 196b for cooperating with flat surfaces 194a and 194b. Cover 185 is similarly equipped. The flat surfaces of the jaws are at about a 35° angle with the horizontal plane.

Inside surfaces of covers 185 and 186 are flat. Covers 185 and 186 have pivoting cam portions 185c and 186c, respectively, which fit over rollers 183d and 184d of bases 183 and 184 when the covers are closed to create sufficient force to flatten the tubing. Pivoting cam portion 186c is held in an up-position about its pivot by friction created by a spring washer (not shown) inserted in pivot hinge 188. Pivoting cam portion 185c is similarly configured. When closing of the mounting blocks is initiated and the flattening jaws of the covers contact the tubes, covers 185 and 186 no longer pivot freely so that cam portions 185c and 186c begin to pivot and engage on rollers 183d and 184d of bases 183 and 184. As the pivoting cam surfaces 185d and 186d engage the rollers, they pull the cover jaws down against the tubes causing the tubes to flatten against lower jaws 193 and 194. When cam portions 185c and 186c are fully pivoted, the tubes are completely flattened and the rollers fully engaged to maintain mounting blocks 180 and 182 closed.

Figure 6:
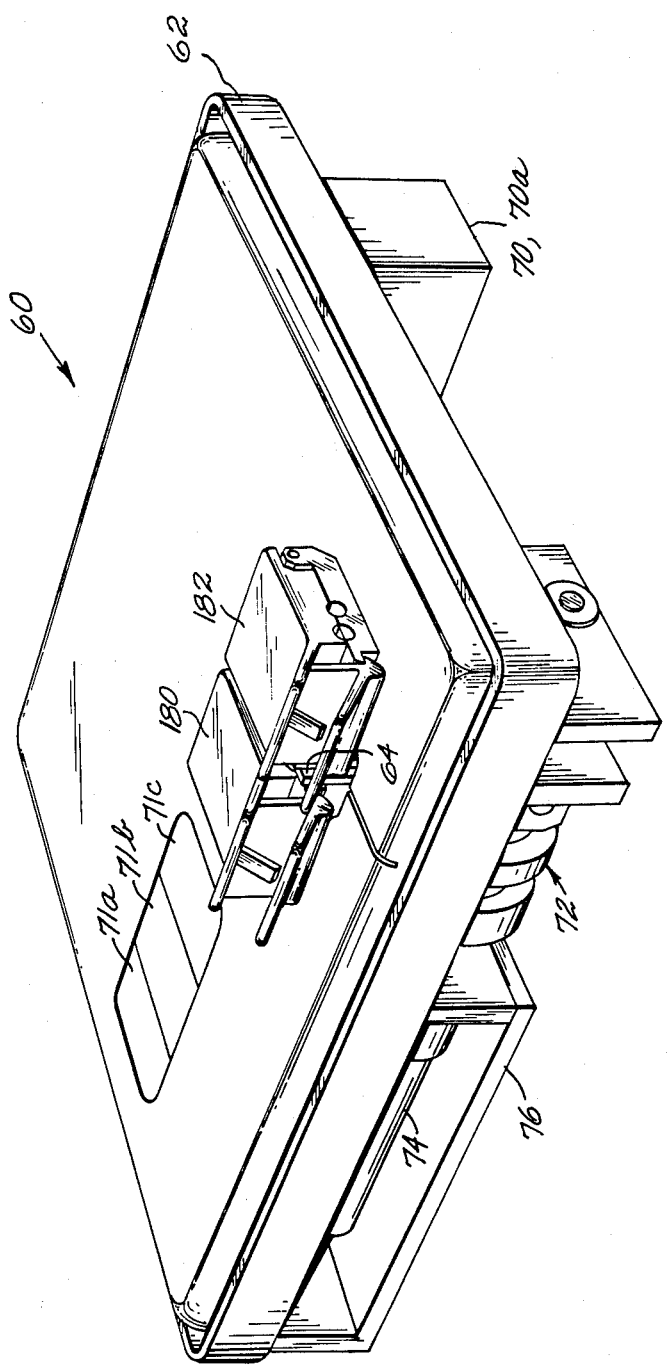
FIG. 6 is an isometric view of an automatic sterile connection device of the invention.

Referring to FIG. 6, the sterile connection device is denoted generally as 60 and includes as major components a housing 62, a cutting mechanism 64 pivotally connected to the housing, a pair of mounting blocks 180 and 182 spaced from each other in the same plane, an evacuation pump 70a driven by a motor 70, a cam cylinder 72 driven by a motor 74 and an electronic control unit 76. The specific embodiment disclosed also includes push buttons 71a, 71b and 71c for checking a battery used for the heating means, for indicating when the system is ready, and for initiating the sterile connection operation, respectively.

Figure 7:
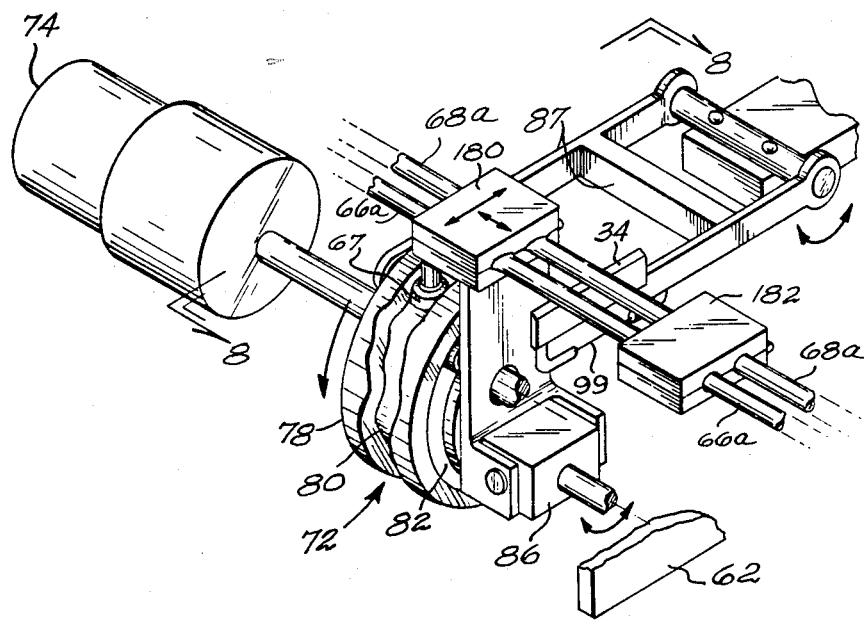
FIG. 7 is an isometric view of the cam used to move the mounting blocks and the cutting means of a sterile connection device of FIG. 6.

FIG. 7 depicts the mechanism for generating the five orthogonal motions required for splicing. More particularly, the mechanism comprises three cams to accomplish the five motions. In the preferred embodiment shown, the cams are grooves 78, 80 and 82 on different faces of cam cylinder 72. This arrangement ensures that the three cams are never out of phase. A cutting element holder 87 for cutting means 34 is pivotally attached to housing 62 at one end and is engaged in cam groove 78 at its other end. The cutting means 34 and heating wire, 99, are positioned between mounting blocks 180 and 182 and below the tubes 66a and 68a held side-by-side in the blocks for splicing. A pivoting block 86 is journaled in housing 62 at one end and journaled to mounting block 180 at its other end. Mounting block 180 intermediate to its ends is engaged in cam groove 82. Mounting block 180 is also engaged in peripheral cam groove 80 via follower 67 while mounting block 182 is fixed to housing 62. Motor 74 rotates cam cylinder 72.

The sterile connection operation with the apparatus disclosed utilizes five orthogonal motions involving mounting block 180, the cutting means 34 and heating wire, 99. These motions are: (1) urging the cutting means 34 through the tubes 66a and 68a; (2) separating cut tube ends; (3) shifting the tubes to align the ones to be joined together; (4) positioning the heating wire 99 (or fluid jet) to transmit heat for sterilization and melting to the tube ends; and (5) urging the tubes together.

As will be appreciated by one skilled in the art, melting the tube ends can be effected after the cutting means is withdrawn up to and during the time the cut ends are being urged together. When the heating means is a hot wire or ribbon, it is preferred that said means be position directly between the severed ends of the tubes to be joined. In this embodiment, the heating means must be removed before the severed tube ends are brought together. Of course, when the heating means is located so as not to interfere with the joining of the tubes, there is no need to remove same during the joining of the tubes.

Fluid jets suitable for use in the present invention are known. Suitable jets are described in *Modern Plastics Encyclopedia*, 1979-80, page 432 and *Plastics Technology*, Bell Communications, Inc. N.Y., 1980-81, page 242. The fluid jet can have a circular or rectangular orifice. Preferably, the orifice is rectangular and has a width of about 0.1 mm to 0.9 mm, most preferably about 0.25 mm. The length of the orifice is preferably about 5 mms. The fluid can be a gas, such as air or an inert gas, a vapor including a vaporized sterilant such as Betadine ® solution, or a flame. Preferably, the fluid is air. The fluid jet, when it is a gas, should be at a pressure of about 10 kPa to 40 kPa, more preferably about 20 kPa to 30 kPa, and most preferably about 24 kPa (3.5 psi).

Figure 8:
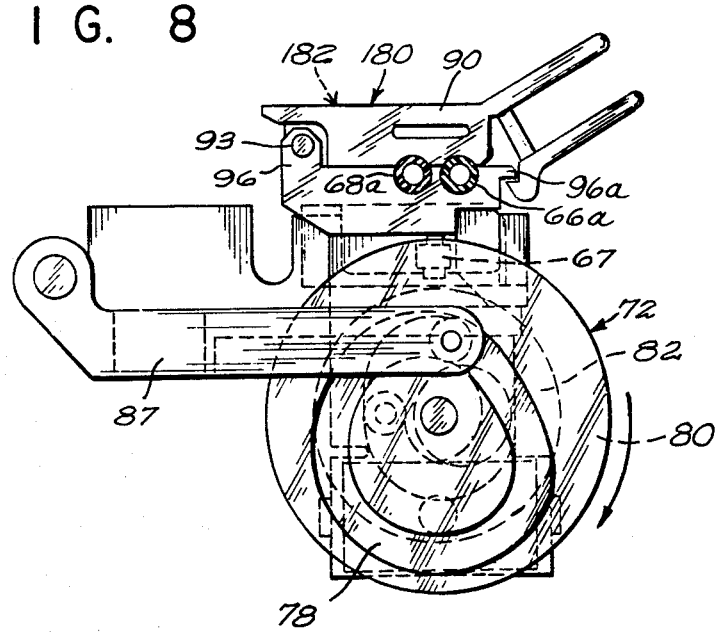
FIG. 8 is a view of FIG. 7 taken along line 8—8.

FIG. 8 depicts cam cylinder 72 rotating in the direction of the arrow and, with this rotation, cam groove 78 lifting the cutting means 34 upwardly through the tubes 66a and 68a. The cut tube ends are then separated by cam groove 80 moving mounting block 180 away from mounting block 182. The tubes to be joined are then aligned by cam groove 82 moving block 180. The heating implement is then positioned by cam groove 78 to effect sterilization/melting and subsequently removed. Continued rotation of the cam cylinder causes peripheral cam groove 80 to urge mounting block 180 toward fixed mounting block 182. Thus, tubes 66a and 68a which are each temporarily sealed are pushed together forming a sterile connection between them. The tubes are removed from the blocks and squeezed to break the temporary seals, thereby effecting fluid communication therethrough.

In the most preferred embodiment of this invention, the stub ends of the tubes are sealed fluid-tight to effect substantially total containment. In this embodiment, prior to being flattened with the mouting blocks, the two tubes are flattened with a clamp in the space between the mounting blocks. All fluid is displaced from the portion of the tubes involved in the sterile connection operation. Employment of a clamp is also useful in situations where the tubing is very stiff. Alternatively, the mounting blocks can be spaced apart a distance which maintains the tubing flat in this section thereby preventing the trapping of liquid. For instance, with tubes of about 5½ mm outside diameter, the spacing between the blocks should be about 0.4 mm to 1 mm, preferably about 0.8 mm. In either mode of operation, the cutting means can be withdrawn prior to alignment of the tubes. The tubes can then be aligned, sterilized/melted, and joined to give a sterile joint.

In a total containment mode, the freshly molten tube ends which are not connected to make a joint emerge with temporary seals which can be made permanent by use of a Hematron ® device. Referring to FIG. 3, one can see that after the ends of tubes 20 and 21 are sterilized/melted by 99 and shifted into alignment, sealed end 12 of tube 20 and sealed end 19 of tube 21 will have temporary seals on the ends. Use of Hematron ® device can be avoided and permanent seals can be effected by either of two other features of the present invention. For example, one of the mounting blocks can be rotated 180° about the central horizontal axis parallel to the axis running through the center of each flattened tube. This rotation brings tubes 20 and 21 and stub ends 12 and 19, respectively, into alignment. After sterilization/melting, heating means, 99, is withdrawn, tubes 20 and 21 are urged together and stub ends 12 and 19 are at the same time urged together to form joints. Each cooled joint can be compressed slightly to provide fluid communication between the joied sections of tubing. Other alternatives to use of a Hematron ® device for obtaining permanent seals in the total containment mode will be obvious to one skilled in the art.

In the description of this invention, the term "seal" has been employed to mean the closure of a tube end; "connection" means the welded joint which holds two tubes together; and "temporary" means that a seal can be opened with light force, i.e., 1 or 2 lbs if the operator so desires but otherwise the seal remains shut. A "temporary seal" may have pinholes. "Fluid-tight temporary seal" means a closure which does not have pinholes and does not permit ingress or egress of fluid. "Stub ends" are the tube ends which are not to be joined. Between a spacing of about 1 mm and 2 mm, preferably about 1½ mm, temporary seals which have no pin holes can be obtained after the heating means is withdrawn. However, some egress of fluid may occur prior to withdrawal. As used herein, "transverse" means across the axis of each tube but not necessarily at a right angle with said axis. The tubes can be flattened in a horizontal, vertical or diagonal plane; howver, a diagonal plane is preferred for convenience when employing a controller operated cam cylinder unit.

The apparatus of the invention can form part of a sterile connection system for continuous ambulatory peritoneal dialysis in which a dialysis solution container with a transfer port that includes a segment of tubing is coupled to a tube extending from an implanted catheter opening into a patient's peritoneal cavity. In this embodiment, the patient's tube and/or the transfer tube can have an entry port with a protective cover or a sealed distal end but preferably both have a sealed distal end. This system minimizes the possibility of peritonitis and permits any other treatment bag, such as a bag of antibiotic, bacteriostat, or other medication to be connected as desired. Moreover, this embodiment offers the additional advantage of eliminating the need for the patient to carry the empty dialysis solution bag because the bag can be sterilely disconnected by using the apparatus of the invention to heat seal both the patient tube and the bag tube. In this mode, a second tube is not placed in the tube slots. The freshly separated tubes are allowed to cool and then, if desired, are permanently sealed by use of a Hematron device.

In the process of the invention, occlusion of the interior of the joined tubes is eliminated and subsequent connections can be made at the same place on a tube. The latter feature provides another aspect of the invention. The CAPD patient has a surgically implanted catheter such as a silastic catheter having an external titanium connector to which a polyvinyl chloride tube having a spike (administration set) is attached. It is necessary to replace the polyvinyl chloride tube about once per month. This replacement provides a source of potential infection of the peritoneum.

In another embodiment, the apparatus of the invention forms part of a sterile connection system for connecting two blood bags. One of the bags can be a donor bag and the other a transfer bag. The donor bag will have a blood collection tube and optionally can have a transfer port with a transfer tube. The transfer bag has a transfer tube (connection tube). The two bags can be sterilely connected by joining the connection tube of the transfer bag to the transfer port of the donor bag. The transfer port of the donor bag can be a conventional entry port having a protective covering and a septum inside the port. The bags can also be connected by joining the blood collection tube of the donor bag to the connection tube of the transfer bag.

In the preferred embodiment for both the blood bag system and the CAPD system, the donor bag and dialysis bag have, specifically for sterile connection, an additional tube (pigtail) which is connector-free and has a sealed dital end. The term "connector-free" as used herein means the tube does not bear any of the conventional fittings, such as a plastic fitting with a diaphragm, a low-melting thermoplastic insert, an insert fusable by radiant energy, or the like. The tube has a sealed distal end which is prepared solely by sealing the tube end together by use of heat, solvent or the like.

In the present system for the sterile connection of blood bags, the need to pre-assemble bags into a system is eliminated. It is to be understood that the expression "blood bag" as used herein refers collectively to either the donor (primary) bag or the satellite bag. With the present invention, satellite bags can be sterilely connected to a donor bag as the need arises.

The apparatus and process of the invention are also useful in other peritoneal dialysis therapies, such as intermittent peritoneal dialysis (IPD), continuous cycled peritoneal dialysis (CCPD), and other therapies using the peritoneal membrane, can beneficially be employed in urinary drainage, and can be used in the manufacture of sterile medical supplies and in other sterile packaging processes. IPD is a machine-automated peritoneal dialysis wherein dialysate is prepared from a concentrate and then delivered to a patient with machine control of inflow and dwell time over a predetermined period of time. CCPD is a machine-automated peritoneal dialysis wherein exchanges of peritoneal fluid are preformed automatically at night and the abdomen is left full during the daytime.

In conventional urinary drainage, an in-dwelling urinary catheter is placed in the bladder/urethra to relieve temporarily anatomic or physiologic urinary obstruction, to facilitate urological surgery, or to permit accurate measurement of urinary output in severely ill patients. The catheter is connected to a drain tube which is connected, in turn, to a urinary drainage bag which is typically accessed three times per day for drainage.

Urinary tract infection is a major risk associated with present urinary drainage procedures, and a strong need for sterile access exists. The device and apparatus of the present invention fulfill that need. The apparatus of the invention when used with suitable disposables can be used for sterile access for bag removal or replacement and for irrigation. The drainage system for this use consists of a Foley catheter connected to a drain tube which is connected to a low-cost disposable drainage bag, additional disposable drainage bags having a connector-free tube specifically for sterile connection and with a sealed distal end; irrigation bags and syringes similary having a connector-free tube with a sealed distal end; and a sterile connection device. Instead of draining the bag three times per day, the used drainage bag can be sterilely disconnected and a new bag sterilely connected thrice daily. For this embodiment, the apparatus of the invention can be employed in the total containment mode.

One example of other sterile packaging processes where the apparatus of the invention can be beneficially employed is in the packaging of sterile milk and fruit juices. In the current commercial production, the contents and package are sterilized separately, then combined in a sterile packaging system. The package includes a drinking straw. Difficulties have been encountered by the consumer in opening the packages and using the drinking straw incorporated therewith.

With the apparatus of the invention the container can be a polyethylene bag with an access port (tube) as the drinking straw. During the packaging operation, the straw can be sterilely and temporarily sealed with the apparatus of the invention. The package can be opened for drinking by application of finger pressure to force open the sterile, temporary seal.

The invention is further illustrated by the following Example in which all percentages are by volume unless otherwise stated.

EXAMPLE

The apparatus used can be a device as depicted in FIG. 5 wherein one mounting block is stationary while the other is pivotably moveable in two orthogonal directions. A cutting means, 0.50 inch (1.27 cm) high and 1.35 inch (3.43 cm) long and 0.012 inch (0.03 cm) thick, can be pivotably held below the tube slots with the 0.012 inch (0.03 cm) dimension centered in the 0.2 inch (0.51 cm) gap between the mounting blocks. The blade can be rigidly supported on each end.

For each joint made, two sections of plasticized polyvinyl chloride tubing with 5.5 mm outside diameter and 0.81 mm thick walls are pressed into the slots. The mounting blocks are closed, thereby flattening each tube in the area of the jaws. The cutting blade is positioned and moved to cut through both flattened tubes simultaneously. The moveable block is then pivotably shifted about 2½ mms to separate the cut tube ends and shifted about 7½ mms to align tube ends to be joined. The blade is then pivotably withdrawn at the same time as a hot wire is positioned near the cut ends. The hot wire is maintained at a temperature of about 500° C. for a period of time sufficient to heat the cut ends and inside tube surfaces back to the clamps to a temperature of about 260° C. for a half second or so.

The moveable block is then pivotably shifted toward the fixed holder to squeeze together the molten tube ends to be joined. The joined tube ends are allowed to cool for several seconds before they are removed from the holders. The flat tube joint then can be popped by manually squeezing the joint between one's fingers. The joined tubes have about 70% of their original strength when pulled in tension and do not leak.

Demonstration of Sterility

Approximately 50 mls of sterile nutrient medium is added to blood bags in a laminar flow laboratory hood with other precautions being taken against bacterial contamination. The nutrient medium contains per liter: 17 g of tripticase peptone (a pancreatic digest of casein), 3 g of phytone peptone (a digest of soybean meal), 5 g of sodium chloride, 2.5 g of dipotassium phosphate and 2.5 g of dextrose. The bags are incubated at 35° C. and after 48 hours the nutrient medium is checked for sterility. There is no evidence of contamination. To guarantee that the sterility test is applied to the inside of the tube, the bags are hung upside down during the incubation period so that the broth is in the tube where the joint is to be made. The outside surface of the blood collection bag tubing is coated with an albumin solution to make the tube sticky and coated with bacteria by immersing the sealed ends of the tubes to a depth of about 4 to 6 inches in a dense bacterial spore suspension ($1.8 \times 10^7$ per ml) of *Bacillus subtillus*, variety *niger (B. globigii)* before the docking is done.

The *B. globigii* spore suspension described above is applied to the ends of the tubing of a plurality of bags containing the nutrient medium and an equal number of empty bags. The tube joining is performed as described above except a wire temperature of about 425° to 485° C. is employed for 15 seconds. The nutrient medium is kept in contact with the joint and incubated for 48 hours. Then, using sterility precautions similar to those described above, the nutrient medium from each bag set is removed and filtered and the filters are incubated for 48 hours at 35° C. The filters so incubated are clean with no evidence of bacteria (indicated by turbidity) thereby demonstrating that live bacteria have not been introduced into the tube lumen during the docking procedure.

I claim:

The embodiments of the invention in which an exclusive property or privilege is claimed are defined as follows:

1. A method for joining thermoplastic tubes together transversely of the axis of each tube comprising:
   (i) flattening a section of each tube to urge inside walls of each tube into contact,
   (ii) cutting through the flattened section of each tube,
   (iii) separating and aligning the tubes to be connected with each other.
   (iv) heating the ends of the aligned tubes to a temperature sufficient to effect tube sterilization and to melt the end surfaces,
   (v) joining the molten ends together, and
   (vi) cooling the joint and effecting fluid communication therethrough.

2. A process for forming a sterile connection between a first and a second closed-end tube, both formed of thermoplastic resin, comprising (a) mounting said tubes in a pair of mounting means which holds said tubes in a flattened, closely adjacent, substantially parallel position, (b) cutting through the flattened part of each of said tubes, (c) separating and aligning said tubes with each other, (d) heating the cut tube ends to effect sterilization and melt the tube ends, (e) urging the desired molten tube ends together to form a joint between said tubes, and (f) cooling said joint and then applying stress to the joint to open the temporary seal in each tube, thereby providing fluid communication between the joined tubes.

3. A process according to claim 2 wherein the tube ends are heated at a temperature and for a time sufficient to effect sterilization.

4. A process according to claim 3 wherein the tube end are heated at a temperature below the temperature where the thermoplastic resin from which the tubes are made begins to degrade in the time used.

5. A process according to claim 4 wherein the mounting means holding the tubes is a pair of blocks having partial grooves therein which hold said tubes, said blocks providing the flattening of said tubes.

6. A process according to claim 4 wherein the tubes to be joined are flattened in step (a) to an extent that fully-closed temporary seals are formed by the heating means.

7. A process according to claim 4 wherein the tubes to be joined are flattened in step (a) to an extent the fluid-tight temporary seals are formed in step (e).

8. A process according to claim 7 wherein, prior to being flattened by the mounting means, the tubes are flattened with a clamp at the point where the heating means passes, said process thereby providing sealed stub-ends.

9. A process according to claim 7 wherein the mounting means are spaced apart a distance such that the tubes to be joined are flattened to an extent that fluid-tight temporary seals are formed in step (e).

10. An apparatus for forming a connection between thermoplastic tubes comprising a cutting means, a pair of mounting blocks adapted to receive, hold and flatten the tubes to be joined, means to provide movement between said blocks and said cutting means to a position such that the cutting means is between said blocks and traversing where the blocks are adapted to receive said tubes, means adapted to separate and realign said blocks to a position where two different tube ends are aligned with and facing each other for each pair of tubes to be joined, means to separate the cutting means from the tubes that have been cut, means for heating the cut ends of the tubes, and means for urging together the tubes to be joined.

11. An apparatus for forming a sterile connection between thermoplastic tubes comprising a cutting means, a heating means, a pair of mounting blocks adapted to receive, hold and flatten the tubes to be joined; means for movement of the mounting blocks to first, second and third positions, the cutting means being between the mounting blocks in the first position, said mounting blocks being relatively displaced in said second position to separate and align two different tube ends facing each other in the location of the heating means, said mounting blocks being separated from said cutting means in said second position, and means for urging said mounting blocks together when in the third position.

12. An apparatus according to claim 11 wherein the means for urging the mounting blocks together is a spring.

13. An apparatus according to claim 11 wherein the means to provide movement between the cutting means, heating means, and the mounting blocks, the means for realigning and the means for urging the blocks together are cam means which provide movement generating five orthogonal motions.

14. An apparatus according to claim 13 wherein the cam means is a driven cam cylinder containing one groove in each face and one groove around its periphery, one of said mounting blocks being coupled to the groove in one face of said cam and to the groove around the periphery of the cam, said cutting and heating means being coupled to the groove in the other face of the cam cylinder, said apparatus having a controller coupled to the cam cylinder to control timing of operation of the apparatus.

15. An apparatus according to claim 11 wherein the mounting blocks comprise upper and lower portions hinged together, the inside surface of each upper portion being flat; partial grooves in said lower portions, said grooves serving to hold the tubes and beginning at a point removed from the proximal edge of each block and increasing in depth as the distal edge of each block is approached.

16. An apparatus according to claim 11 wherein the blocks are adapted to receive two tubes.

17. An apparatus according to claim 16 wherein the blocks are urged together as the heating means is withdrawn.

18. An apparatus according to claim 16 wherein the blocks are urged together after the heating means is withdrawn.

19. An apparatus according to claim 11 wherein the blocks are adapted to receive three tubes.

20. A sterile connection system for continuous ambulatory peritoneal dialysis in which a dialysis solution container with a transfer port that includes a segment of tubing is coupled to a tube extending from a patient's peritoneal cavity, wherein the improvement comprises a pair of mounting blocks adapted to receive, hold and flatten the transfer port tube and the patient's tube, cold-cutting means, means to provide movement between said blocks and said cutting means to a position such that the cutting means is between said blocks and traversing where the blocks are adapted to receive said tubes, means to realign said blocks to a position where the resulting different tube ends to be joined are aligned with and facing each other, means to separate the cutting means from the tubes that have been cut, means for heating the cut ends of the tubes, and means for urging together the tubes to be joined.

21. A sterile connection system according to claim 20 wherein the blocks are urged together as the heating means is withdrawn.

22. The sterile connection system according to claim 21 wherein the patient's tube is connectorfree and has a sealed distal end.

23. The sterile connection system according to claim 22 wherein the transfer port tube is connector-free, has a sealed distal end, and is the same diameter as that of the patient's tube.

24. A sterile connection system for joining two blood bags, each bag having a tube which can be used for connection and sterile connection being made by joining said tubes, wherein the improvement comprises a pair of mounting blocks adapted to receive, hold and flatten the tubes to be joined; cold-cutting means; means to provide movement between said blocks and said cutting means to a position such that the cutting means is between said blocks and traversing where the blocks are adapted to receive said tubes; means to realign said blocks to a position where the resulting two different tube ends to be joined are aligned with and facing each other; means to separate the cutting means from the tubes that have been cut, means for heating the cut ends of the tubes, and means for urging together the tubes to be joined.

25. A sterile connection system according to claim 24 wherein the blocks are urged together after the heating means has been withdrawn.

26. The sterile connection system according to claim 25 wherein one of the bags is a donor bag and its blood collection tube is one of the tubes to be joined.

27. The sterile connection system according to claim 26 wherein the two tubes to be joined are of the same diameter.

28. The sterile connection system according to claim 27 wherein the blood collection tube has a sealed distal end.

29. The sterile connection system according to claim 28 wherein the second bag is a transfer bag having a transfer port with a transfer tube and the transfer tube is the other tube to be joined.

30. The sterile connection system according to claim 29 wherein the transfer tube has a sealed distal end.

31. The sterile connection system for urinary drainage in which a first drainage container is connected to a drainage tube extended from a catheter implanted in a patient's urethra, wherein the improvement comprises (a) a second drainage container having a connector-free tube specifically for sterile connection and with a sealed distal end, both containers being disposable; and (b) a pair of mounting blocks adapted to receive, hold and flatten the drainage tube and the connector-free tube, cold-cutting means, means to provide movement between said blocks and said cutting means to a position such that the cutting means is between said blocks and traversing where the blocks are adapted to receive said tubes, means to realign said blocks to a position where the resulting different tube ends to be joined are separated and aligned with and facing each other, means to separate the cutting means from the tubes that have been cut, means for heating the cut ends of the tubes, and means for urging together the tubes to be joined.

* * * * *